United States Patent [19]

Sieja

[11] Patent Number: 5,153,351
[45] Date of Patent: Oct. 6, 1992

[54] REMOVAL OF TETRAHYDROAZEPINE (THA) FROM 6-AMINOCAPRONITRILE BY REACTION WITH REACTIVE METHYLENE COMPOUNDS

[75] Inventor: James B. Sieja, Wilmington, Del.

[73] Assignee: E. I. Du Pont de Nemours and Company, Wilmington, Del.

[21] Appl. No.: 817,086

[22] Filed: Jan. 6, 1992

[51] Int. Cl.$^5$ .......................................... C07C 253/34
[52] U.S. Cl. ........................................ 558/452; 203/38
[58] Field of Search ............... 558/452, 454, 456, 457

[56] References Cited

U.S. PATENT DOCUMENTS

| | | | |
|---|---|---|---|
| 2,242,309 | 5/1941 | Lazier et al. | 558/456 |
| 2,305,103 | 12/1942 | Osgood | 558/456 |
| 3,004,059 | 10/1961 | Wüst | 558/452 |
| 3,177,242 | 4/1965 | Adam et al. | 558/456 |
| 3,616,269 | 10/1971 | Aelony et al. | 558/456 X |
| 3,655,721 | 4/1972 | Arni et al. | 558/456 X |

FOREIGN PATENT DOCUMENTS

| | | | |
|---|---|---|---|
| 601619 | 7/1960 | Canada | 558/452 |
| 43-4494 | 2/1968 | Japan | 558/452 |
| 45-12849 | 5/1970 | Japan | 558/452 |

OTHER PUBLICATIONS

Fieser et al., Advanced Organic Chemistry, (1961), p. 478.

Primary Examiner—Joseph Paul Brust
Attorney, Agent, or Firm—Earl L. Handley

[57] ABSTRACT

A mixture containing 6-aminocapronitrile is purified by reacting the tetrahydroazepine contained therein with a methylene compound, and then distilling the 6-aminocapronitrile from the resulting mixture.

3 Claims, No Drawings

REMOVAL OF TETRAHYDROAZEPINE (THA) FROM 6-AMINOCAPRONITRILE BY REACTION WITH REACTIVE METHYLENE COMPOUNDS

FIELD OF THE INVENTION

This invention relates to the preparation of purified 6-aminocapronitrile from a mixture containing tetrahydroazepine (THA) by converting the THA to higher boiling compounds and then recovering 6-aminocapronitrile by controlled distillation. The 6-aminocapronitrile is then sufficiently pure to be polymerized to a high molecular weight 6-nylon having good color and low gel content.

BACKGROUND OF THE INVENTION

The polymerization of 6-aminocapronitrile to form nylon polymer is disclosed in Greenewalt U.S. Pat. No. 2,245,129, and Curatolo et al. U.S. Pat. No. 4,586,736.

When 6-aminocapronitrile is produced by partial hydrogenation of adiponitrile, hexamethylenediamine and tetrahydroazepine (THA), are coproduced. THA is represented by the formula:

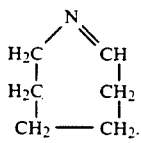

The hexamethylenediamine is easily removed from the mixture by simple distillation, but THA is not easily separated. The presence of THA in the 6-aminocapronitrile (hereinafter sometimes referred to as 6-ACN) that is to be polymerized limits the molecular weight of the polymer and causes color and branching in the polymer. It is, therefore important that THA be removed from the 6-ACN before polymerization.

It is an object of the present invention to provide a simple and efficient method of obtaining 6-ACN that is free from THA.

SUMMARY OF THE INVENTION

The present invention is a process for the recovery of 6-ACN from a mixture with tetrahydroazepine which comprises reacting a methylene compound selected from the group consisting of malonitrile, dicyclopentadiene, cyclopentadiene, nitromethane, nitroethane, and indene with the tetrahydroazepine in the mixture and then distilling 6-ACN from the resulting mixture.

DETAILED DESCRIPTION

6-ACN can be produced by partial hydrogenation of adiponitrile. Hexamethylenediamine (HMD) and small quantities of tetrahydroazepine (THA) are coproduced. HMD is easily removed by simple distillation. THA, however, cannot be removed by simple distillation. It is important that THA be removed, since it limits molecular weight and causes color and branching during polymerization of 6-ACN to nylon 6.

Addition of certain reactive methylene compounds to 6-ACN contaminated with THA, converts the THA into products which can be separated by simple distillation.

Effective Reactive Methylene Compound

Ordinarily, one would define the reactivity of useful materials in terms of the compounds which function in the so-called Knoevenagel reaction, "the base catalyzed reaction of an aldehyde with malonic acid and other compounds having a methylene group activated by carbonyl, nitrile, or nitro groups" (from Fieser and Fieser, Advanced Organic Chemistry, 1961, page 478). However, reaction with dimethyl malonate or ethyl acetoacetate, which are successful Knoevenagel substrates, fail in this application. Methylene compounds selected from the group consisting of malonitrile, dicyclopentadiene, cyclopentadiene, nitromethane, nitroethane, and indene are satisfactory.

Reaction Time and Temperature

Each effective methylene compound requires its own specific conditions. The reaction is complicated since the initial reaction is almost certainly reversible, but after a time, especially if the reaction mixture is heated, the reaction results in products which may not be reversed back to THA.

Temperature as low as room temperature is satisfactory for some methylene compounds—see example 2 below. Temperature as high as 200 degrees C. are satisfactory for other methylene compounds.

It is usually desirable to have the methylene compound in the reaction mixture in an amount at least stoichiometrically equivalent to the amount of THA in the reaction mixture. Large excesses of the methylene compound are not desirable. The amount of methylene compound for most mixtures of 6-ACN and THA is usually about 0.1 to 10 % by weight of the reaction mixture.

Distillation of the 6-ACN from the reaction mixture after the THA is through reacting is best accomplished at pressures less than atmospheric. At higher pressures higher temperatures are required, and the 6-ACN sometimes forms undesirable byproducts under these conditions. The distillation is best accomplished at temperatures of less than about 200 degrees C., and preferably less than about 165 degrees C.

In the case of dicyclopentadiene, it is contemplated that a large scale process would include the following: The THA-contaminated 6-ACN would be mixed with a couple % dicyclopentadiene (the form in which it is readily available) and fed to a distillation pot in excess of about 170 degrees C. (the temperature where dicyclopentadiene is converted to the reactive monomeric form), and the excess monomeric cyclopentadiene taken overhead. The THA-cyclopentadiene reaction products would form high boilers which are occasionally purged. THA-free 6-ACN is taken as a heart cut. A further rectification of the 6-ACN may be required. The unreacted cyclopentadiene can be fed back into the system as the monomer, or allowed to dimerize and then put back into the system.

DETAILED EXAMPLES

Example 1

1 g of malononitrile was added to 11 g of 6-ACN containing 0.45% THA. The temperature was raised to 60 degrees C. The first sample was taken at 30 degrees C. before heating had begun, and subsequent samples were taken at 1, 3, and 5 hours after the mixture had reached 60 degrees. Analysis measured 0.028, 0.01, 0.0, and 0.0% THA. Thus most of the reaction had proceeded at 30 degrees C. before the first sample had been taken.

Example 2

A mixture of 100 g of 6-ACN containing 0.45% THA and 1 g of malononitrile was stirred at 25 degrees C. for 63 hours. A sample was taken after 20 minutes and showed the THA to be 0.059%. After 63 hours, the 6-ACN was distilled at 0.25 mm mercury. THA in the distillate measured <0.005%.

Example 3

A mixture of 100 g of 6-ACN containing 0.45% THA and 1 g of malononitrile was stirred overnight at room temperature. Half of it was distilled at 0.5 mm mercury, and half at 25 mm mercury. The first distillate contained 0.006% THA, and the second 0.033% THA. The result indicates that lower distillation temperatures give lower THA in the distillate.

Example 4

A mixture of 98 g of 6-ACN containing 0.45% THA and 2 g dicyclopentadiene was heated to 100 degrees C. After 1 hr., the THA still measured 0.31%. The temperature was increased to 150 degrees C., and after an hour, the THA measured 0.013%. Since the temperature of decomposition of dicyclopentadiene to cyclopentadiene monomer is near 150 degrees C., it was surmised that the active form is the monomer. After 3 hours at 150 degrees the THA measured 0.009%. Half of the mixture was distilled at 0.5 mm mercury, and half at 20 mm. The first distillate measured 0.005% THA and the second 0.024% THA.

Example 5

A mixture of 98 g of 6-ACN containing 0.45% THA and 2 g of freshly prepared cyclopentadiene monomer was stirred at room temperature. Immediately after mixing, the THA measured 0.047% THA. After 1 hr., THA measured 0.025%, and after 4.5 hours, 0.025%. After stirring a total of 19 hours, half of the 6-ACN was distilled at 0.5 mm mercury, and half at 25 mm. The first distillate measured 0.017% THA, the second 0.132%.

Example 6

A mixture of 98 g of 6-ACN containing 0.45% THA and 2 g dicyclopentadiene was heated at 170 degrees C. for 2 hours. Samples were taken at 0, 1 and 2 hr. after 170 degrees had been reached. THA measured 0.164%, 0.016%, and <0.005%. Half of the 6-ACN was distilled at 0.5 mm mercury, and half at 25 mm. The first distillate measured 0.005% THA, and the second 0.02% THA. This again demonstrates that the lower temperature distillation gives a distillate lower in THA concentration. It also demonstrates that longer times at higher temperatures allows distillation at higher temperature (compare to second distillate of example 5).

Control for Example 6

Distillation of 6-ACN containing 0.38% THA was distilled at 25 mm mercury. The distillate contained 0.34% THA.

Example 7

A mixture of 11 g of 6-ACN containing 0.49% THA and 1 g nitroethane was stirred at 60 degrees C. for 7 hours. Samples were taken at 0, 1.25, 1.75, and 4.75 hours. The 0 hr. sample was taken at 25 degrees just after mixing. The other samples were taken at the time after 60 degrees C. was reached. THA measured 0.40, 0.20, 0.12, and 0.07%.

Example 8

A mixture of 98 g of 6-ACN containing 0.45% THA and 2 g nitroethane was stirred at 25 degrees C. over 3 days. Samples were taken at 0, 1, and 72 hours. THA measured 0.137%, 0.16%, and 0.057%. Half of the 6-ACN was distilled at 0.5 mm mercury, and half at 100 mm. THA in the distillates measured 0.044% and 0.017%.

Example 9

A mixture of 11 g of 6-ACN containing 0.49% THA and 1 g of nitromethane was stirred at 60 degrees C. overnight. Samples 0 and 1 were taken at 25 degrees and 54 degrees respectively. Samples 2-7 were taken after the temperature reached 60 degrees at times 0, 1, 3, 4.5, 7.5, 22 hours. THA for samples 0, 1, 2, 3, 4, 5, 6, and 7 measured 0.38, 0.16, 0.11, 0.06, 0.02, 0.017, 0.007, and 0.006%. Distillation at 0.2 mm mercury gave 6-ACN containing <0.005% THA.

Example 10

A mixture of 98 g of 6-ACN containing 0.45% THA and 2 g nitromethane was stirred at 25 degrees C. over 3 days. Samples were taken at 3, 6, and 72 hours. THA measured 0.12%, 0.12%, and 0.024%. Half of the 6-ACN was distilled at 0.5 mm mercury, and half at 100 mm. THA in the distillates measured 0.013% and 0.019%.

Example 11

A mixture of 98 g of 6-ACN containing 0.45% THA and 2 g 2-amino-1-propene-1,1,3-tricarbonitrile (malononitrile dimer) was stirred at 25 degrees C. for 3 hours. Samples were taken at 0, 1, 2, and 3 hours. THA measured 0.059%, 0.04%, 0.04%, and 0.05%. Half of the 6-ACN was distilled at 0.5 mm mercury, and half at 100 mm. The THA in the distillate measured 0.013% and 0.057%.

Example 12

A mixture of 100 g of 6-ACN containing 0.19% THA and 2 g indene were heated to 100 degrees for 5 hours. Samples were taken at 0, 1, 3.5, and 5 hours. All samples were at 100 degrees C. before sampling. THA analyses for these samples measured 0.19, 0.064, 0.029, and 0.029%.

Example 13

A mixture of 300 g of 6-ACN containing 0.19% THA and 6 g of indene was heated at 125 degrees C. for one hour. At this time the THA measured 0.043%. Some of the mixture was poop-distilled at 20 mm mercury to give 4 cuts. The THA in the cuts measured 0.13%, 0.16%, 0.16%, and 0.16%. The weight of each cut was 18.6, 7.15, 19.6, and 19.3 g. The pot remaining after the four cuts were taken measured 0.14% THA. This demonstrates that the reaction with indene is reversible if not preheated at a high enough temperature before distillation.

Example 14

The pot from example 13 was treated with 6 more grams of indene, and heated to 200 degrees C. for three hours. At this time the THA measured 0.015%. The 6-ACN was distilled at 20 mm mercury, and three cuts were taken. The cuts weighed 111 g, 92 g, and 11 g. The THA measured, 0.005, 0.024, and 0.038%, respectively.

I claim:

1. A process for the recovery of 6-aminocapronitrile from a mixture containing 6-aminocapronitrile and tetrahydroazepine which comprises reacting a methylene compound selected from the group consisting of malonitrile, dicyclopentadiene, cyclopentadiene, nitromethane, nitroethane, and indene with the tetrahydroazepine in the mixture and then distilling 6-aminocapronitrile from the resulting mixture.

2. The process of claim 1 in which the compound is malonitrile.

3. The process of claim 1 in which the reaction is at atmospheric pressure.

* * * * *